United States Patent [19]
Conger et al.

[11] Patent Number: 6,104,961
[45] Date of Patent: Aug. 15, 2000

[54] ENDOCARDIAL DEFIBRILLATION LEAD WITH LOOPED CABLE CONDUCTOR

[75] Inventors: Steven Conger, Agua Dulce, Calif.; Stephen L. Goldman, Missouri City; G. Shantanu Reddy, Houston, both of Tex.

[73] Assignee: Intermedics Inc., Angleton, Tex.

[21] Appl. No.: 09/252,503

[22] Filed: Feb. 18, 1999

[51] Int. Cl.[7] ................................................ A61N 1/05
[52] U.S. Cl. ............................................................. 607/122
[58] Field of Search ................................. 607/116, 117, 607/119, 122, 123

[56] References Cited

U.S. PATENT DOCUMENTS

| | | | |
|---|---|---|---|
| 4,830,006 | 5/1989 | Haluska et al. | 128/419 PG |
| 4,922,927 | 5/1990 | Fine et al. | 128/786 |
| 5,040,534 | 8/1991 | Mann et al. | 128/419 PG |
| 5,314,453 | 5/1994 | Jeutter | 607/61 |
| 5,374,287 | 12/1994 | Rubin | 607/131 |
| 5,476,502 | 12/1995 | Rubin | 607/127 |
| 6,006,139 | 12/1999 | Kruse et al. | 607/125 |

*Primary Examiner*—Scott M. Getzor
*Attorney, Agent, or Firm*—Schwegman, Lundberg, Woessner & Kluth, P.A.

[57] ABSTRACT

An implantable endocardial defibrillation lead having a looped cable conductor for conducting at least high voltage defibrillation shocks. A coil electrode is connected to an elongated, flexible, electrically non-conductive lead body and is supplied with electrical power for delivering electrical shocks to the heart through a looped cable conductor that extends through the lead body and is associated with a power source.

34 Claims, 8 Drawing Sheets

ENDOCARDIAL DEFIBRILLATION LEAD WITH LOOPED CABLE CONDUCTOR

BACKGROUND OF THE INVENTION

1. Field of the Invention

The present invention relates generally to implantable cardiac stimulation devices and systems for regulating the contraction of a heart. More particularity, the invention relates to a defibrillation lead, and more particularly to a defibrillation lead having a cable-type electrical conductor.

2. Description of the Related Art

Implantable medical devices for treating irregular contractions of the heart with electrical stimuli are well known in the art. Some of the most common forms of such implantable devices are defibrillators and pacemakers.

Defibrillators are implantable medical devices used to treat fibrillation, a condition characterized by rapid, chaotic electrical and mechanical activity of the heart's excitable myocardial tissue that results in an instantaneous cessation of blood flow from the heart. Defibrillation is a technique employed to terminate fibrillation by applying one or more high energy electrical pulses to the heart in an effort to overwhelm the chaotic contractions of individual tissue sections and to restore the normal synchronized contraction of the total mass of tissue.

A pacemaker, or pacer, is an implantable medical device that delivers low energy electrical pulses to stimulate a patient's heart to beat at a desired rate in instances where the heart itself is incapable of proper self-regulation. This occurs when the heart's natural pacemaker, which causes the rhythmic electrical excitation of the heart and pumping of blood, malfunctions due to age or disease. Demand pacing is a process used to maintain normal beating of a heart having this condition.

Various types of leads for defibrillators and demand pacers have been suggested in the prior art. For example, large electrical patches sewn to the exterior surface of the heart have been used to deliver defibillation pulses to the heart. Implantation of such patch electrodes requires opening of the patient's chest during thoracic surgery. For pacing, pulses may be applied to the heart with the use of a pacer lead having an exposed metal surface, or demand pacer electrode, extending through a vein and into the heart.

Those involved in the medical arts recognized that prior art defibrillators required a high threshold level of energy for effective defibrillation, which limited the useful life-span of the devices and, more significantly, posed a significant risk of causing electrolysis of the blood and myocardial damage. It was realized that the defibrillation electrode configuration played an important role in the amount of energy needed to achieve successful defibrillation. This led to the development of transvenous defibrillation leads having long coil-shaped defibrillation electrodes for implantation into the right ventricle of the heart through a vein. For example, U.S. Pat. No. 4,922,927, the entire disclosure of which is incorporated herein by reference, discloses a defibrillation electrode made up of a plurality of separate wires wound side-by-side to form a tight coil. The coil was disposed upon an insulated tubular member and had a length sufficient to extend throughout the entire length of the ventricular chamber to provide sufficient electrode surface area for defibrillation.

Transvenous cardiac stimulation leads, such as the device of U.S. Pat. No. 4,922,927, were configured to also carry a demand pacing electrode. Thus, a single device implantable in one surgical procedure could provide defibrillation and pacing pulses for heart patients suffering from both irregular heart beat and, at times, cardiac fibrillation. This eliminated the need for multiple and complex surgical procedures to attach the prior art electrodes required for both types of treatments.

Another defibrillation electrode configuration for use with dual purpose transvenous leads is disclosed in U.S. Pat. Nos. 5,476,502 and 5,374,287 to Rubin, which are also incorporated herein by reference in their entireties. The "Rubin" catheter included either a helical or lance shaped defibrillation electrode for delivering a defibrillation pulse directly to the interior of the septum of the patient's heart. The length of the helix-shaped electrode to be screwed into the septum from the right ventricle, about 0.5 cm to 1.0 cm, was substantially shorter than the conventional coiled transvenous defibrillation electrodes.

Despite these developments there continues to be a need for a lead capable of providing both high voltage defibrillation and effective demand pacing with a smaller lead diameter to minimize obstruction in the veins leading to the heart.

SUMMARY OF THE INVENTION

In accordance with the present invention, there is provided an implantable endocardial defibrillation lead having a looped cable conductor for conducting at least high voltage defibrillation shocks. A coil electrode is connected to an elongated, flexible, electrically non-conductive lead body and is supplied with electrical power for delivering electrical shocks to the heart through a looped cable conductor that extends through the lead body and is associated with a power source.

Depending upon the desired application for the lead, the invention may also be used with a pacer and, thus, include any of a variety of pacer electrodes and sensors that are presently available or may become available. Such devices, if used, would be disposed upon the lead, insulated from the defibrillator electrode segments and electrically connected with a second electrical conductor that extends through the lead body and provides electrical power to the pacer electrode. The lead may also include a ground electrode disposed upon the lead a distance from the other electrodes to receive the pulses delivered to the heart tissue and transmit them back through a third electrical conductor extending through the lead. The coil electrode and looped cable conductor may also serve a dual function as a ground electrode and conductor.

The invention may also be adapted for fixation of the distal end of the lead to the heart to achieve selective positioning of the electrode or electrodes. A variety of currently available passive and active fixation mechanisms, or that may become available, may be used with the invention. For example, the lead may include tines. A small fixation screw for securing the distal end of the lead within the heart could also be used.

The present invention also provides a system for regulating the beating of a heart. The system includes the lead, as previously discussed, attached to a pulse generator at the proximal end of the lead. In the preferred embodiment, the pulse generator includes a processor, a defibrillator circuit, and a pacer circuit. The processor senses and analyzes the natural electrical charge created by the heart. Depending upon the results of the analysis, the processor informs the pacer circuit or defibrillator circuit to discharge either a demand pulse or a defibrillation shock, respectively. The pulse then travels down the appropriate electrical conductor and is discharged to the heart through the appropriate defibrillation or pacer electrode.

It is therefore an object of the present invention to provide an endocardial defibrillation lead with a looped cable conductor. Another object of this invention is to minimize the diameter of a defibrillation lead. It is also an object of this invention to provide methods and apparatus for regulating the beating of a heart. It is another object of the present invention to provide a single apparatus that can effectively deliver both defibrillator and pacer pulses to a heart.

The characteristics and advantages of the present invention described above, as well as additional features and benefits, will be readily apparent to those skilled in the art upon reading the following detailed description and referring to the accompanying drawings.

BRIEF DESCRIPTION OF THE DRAWINGS

For a detailed description of the preferred embodiments of the invention, reference will now be made to the accompanying drawings wherein.

DETAILED DESCRIPTION OF THE PREFERRED EMBODIMENTS

The presently preferred embodiments of the invention are shown in the above-identified figures and described in detail below. In describing the preferred embodiments, like or identical reference numerals are used to identify common or similar elements. The figures are not necessarily to scale and certain features and certain views of the figures may be shown exaggerated in scale or in schematic form in the interest of clarity and conciseness.

Figure 1:
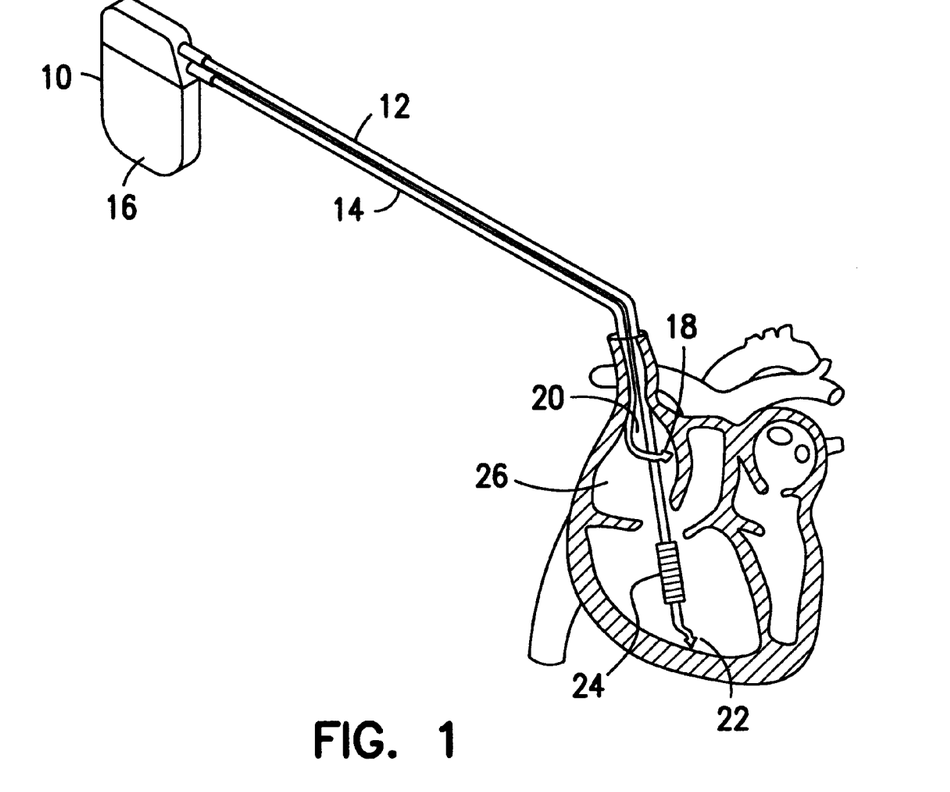
FIG. 1 is a perspective view of an implantable cardioverter/defibrillator ("ICD") with a defibrillation and pacer lead of the present invention.

Referring now to FIG. 1, an implantable medical device 10 constructed in accordance with the preferred embodiment is shown implanted and coupled, in an exemplary configuration, to the patient's heart by leads 12, 14. The implantable medical device 10 may include a cardioverter/defibrillator, combination cardioverterldefibrillator and pacemaker, or any other device that provides pacing support for the patient's heart. For purposes of describing the preferred embodiments of the invention, however, the implantable medical device 10 will hereafter be described as an implantable cardioverter/defibrillator ("ICD") with the understanding that pacemaker functions are also included. However, it should be understood that the invention may be employed in any of a variety of implantable medical devices, including simple pacemakers.

The arrangement shown in FIG. 1 represents a dual chamber pacing configuration in which two leads 12 and 14 are coupled to a housing or "can" 16 of the ICD. In the configuration shown, the leads are positioned in two chambers of the heart, one lead 12 implanted in the right ventricle and the other lead 14 implanted in the right atrium. Each lead may incorporate any desired number of electrodes. The leads 12, 14 shown in FIG. 1, for example, are bipolar leads, meaning each lead includes two electrodes. Lead 14 includes a tip cathode electrode 18 and a ring anode electrode 20. Lead 12 includes a tip cathode electrode 22 and a shock coil 24 for delivering a defibrillation shock pulse. Some ICD leads include tip and ring electrodes as well as a shock coil. As one skilled in the art will understand, two, three, and four lead devices that have been used or suggested as various pacemaker or ICD configuration schemes in other applications may be employed in the present invention. Further, the ICD housing 16 itself can be used as an electrode. The configuration shown in FIG. 1 is intended to be exemplary only of the many lead configurations possible for ICD 10.

ICD 10 may also communicate with an external programmer (not specifically shown). If it is desired for the ICD 10 to include a communication capability, any one of a number of communication techniques may be used. Preferably, however, the communication technique used involves wireless transmission of control and data signals, such as that disclosed by U.S. Pat. No. 5,314,453, incorporated herein by reference.

Figure 2:
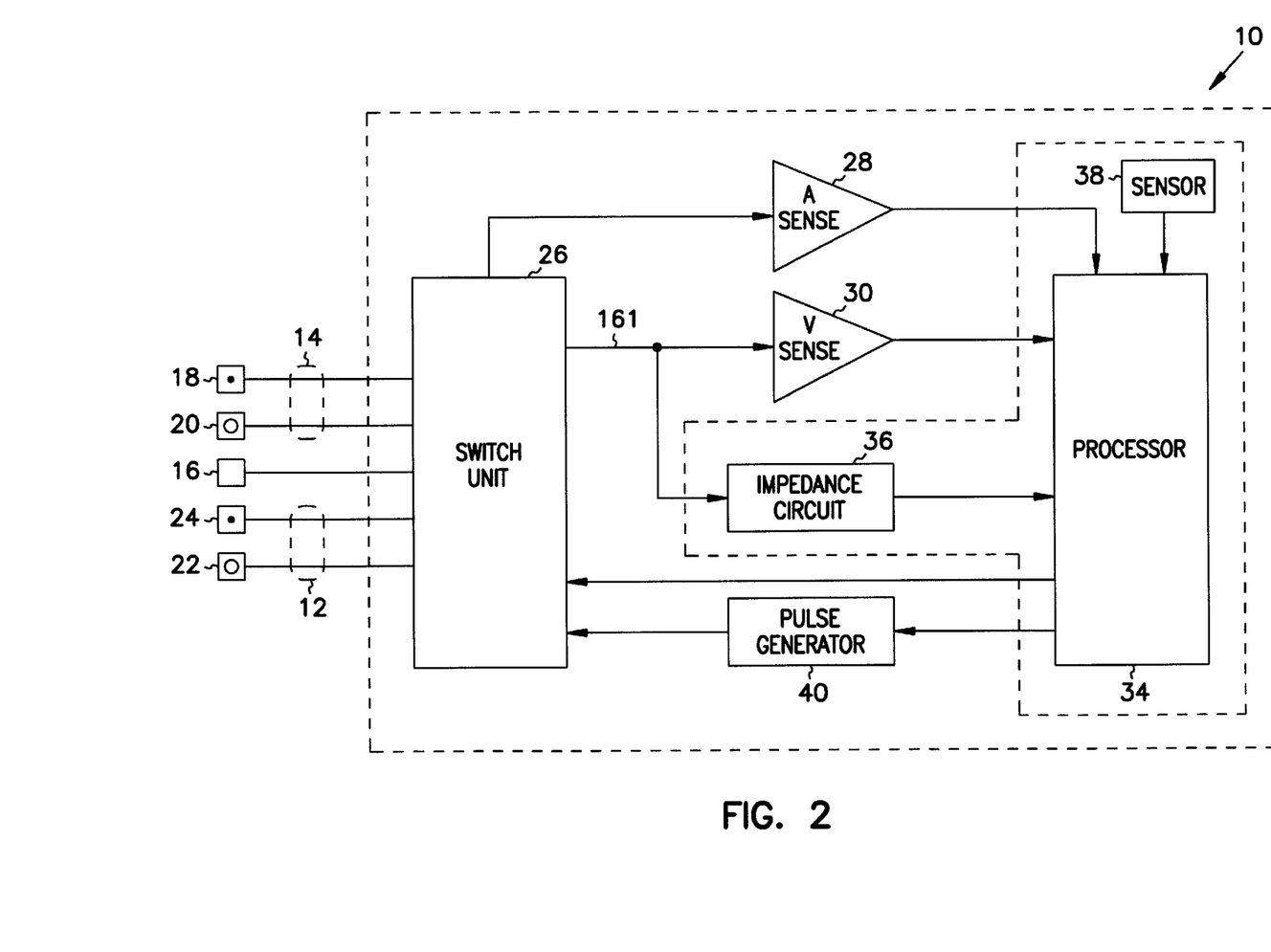
FIG. 2 is a schematic diagram of the ICD of FIG. 1.

The preferred embodiment of the ICD 10 is illustrated in the exemplary block diagram of FIG. 2. The ICD 10 generally includes a switch unit 26, atrial and ventricular sense circuits 28, 30, a heart status monitor 32 which includes a processor 34 and an impedance circuit 36 and/or a sensor 38, and a pulse generator 40. The exemplary embodiment of FIG. 2 shows ICD 10 with five electrodes, namely atrial tip and ring electrodes 18 and 20, ventricular shock coil and tip electrodes 24, 22, and can electrode 16. The invention, however, may be practiced using any number of electrodes implanted in any chamber of the heart.

Referring still to FIG. 2, the atrial sense circuit 28 processes signals received from the atrial chamber of the heart via the atrial electrodes 18, 20 and the ventricular sense circuit 30 processes signals from the ventricular chamber via the ventricular electrodes 22, 24. The atrial and ventricular sense circuits 28, 30 generally include a low power, highly sensitive amplifier, a band pass filter, and a threshold detector (not specifically shown). The amplifier amplifies the electrical signal from the associated electrodes, and the band pass filter attenuates signals whose frequencies are outside the range of frequencies known to correspond to cardiac signals. The threshold detector compares the amplified and filtered signal to a reference signal to determine when a cardiac event (also referred to as a "sense event") has occurred. If the magnitude of the amplified and filtered cardiac signal exceeds the reference signal, the processor 34 determines that a sense event has occurred. The processor 34 may then pace the heart based either on detecting or not detecting sense events. For example, the processor 34 may initiate a ventricular pacing pulse if a ventricular sense event has not been detected within a predetermined period of time following a previous atrial sense event.

The pulse generator 40 is employed to produce an appropriate electrical pulse to stimulate the desired chamber of the heart to beat. The processor 34 initiates the pulse generator 40 to produce a pacing pulse, and the pulse generator responds by delivering the pacing pulse to the desired chamber of the heart. The pulse generator may include a rate limiter to prevent the processor 34 from erroneously pacing the heart at an excessively high rate.

Switch unit 26 preferably includes multiple solid state switches (not specifically shown) and preferably one switch connects to each electrode. The states of the switches are controlled by processor 34 via control lines 42. The processor 34 controls the state of switch unit 26 to connect the electrodes to either the sense circuits 28, 30 or the pulse generator 40. Further, the processor 34 may control the state of each switch contained within switch unit 26 independently of other switches that may be contained within switch unit 26. The processor 34 connects the desired electrodes (either the atrial electrodes 18, 20 or the ventricular electrodes 22, 24) to pulse generator 40 when the processor desires to initiate a pacing pulse to the appropriate atrial or ventricular chamber. The processor 34 may also be employed to sense the electrical activity in either the atrial or ventricular chambers, or both, by altering the state of switch unit 26 to connect the desired electrodes to the corresponding sense circuit 28, 30.

The ICD 10 preferably operates in a predetermined pacing mode that is suitable for the patient. Accordingly, ICD 10 may be programmed to operate in one of a number of pacing modes. For example, the ICD 10 may be programmed to sense electrical activity in the atrium, and then to pace the ventricle following a predetermined time delay after the atrial sense event if the ventricle has not beat on its own.

The ICD 10 may be implanted within or maintained external to the body of the patient. The structure, function, and components, such as a power supply and circuitry, of the pulse generator are well known in the art. U.S. Pat. Nos. 4,830,006 and 5,040,534, the entireties of which are incorporated herein by reference, disclose preferred circuitry and components for ICD 10 for delivering pacing and defibrillating pulses. The lead and ICD 10 together comprise a system that is capable of controlling the beat of the heart of the patient by delivering to the heart electrical pulses of appropriate energy level and duration.

Figure 3:
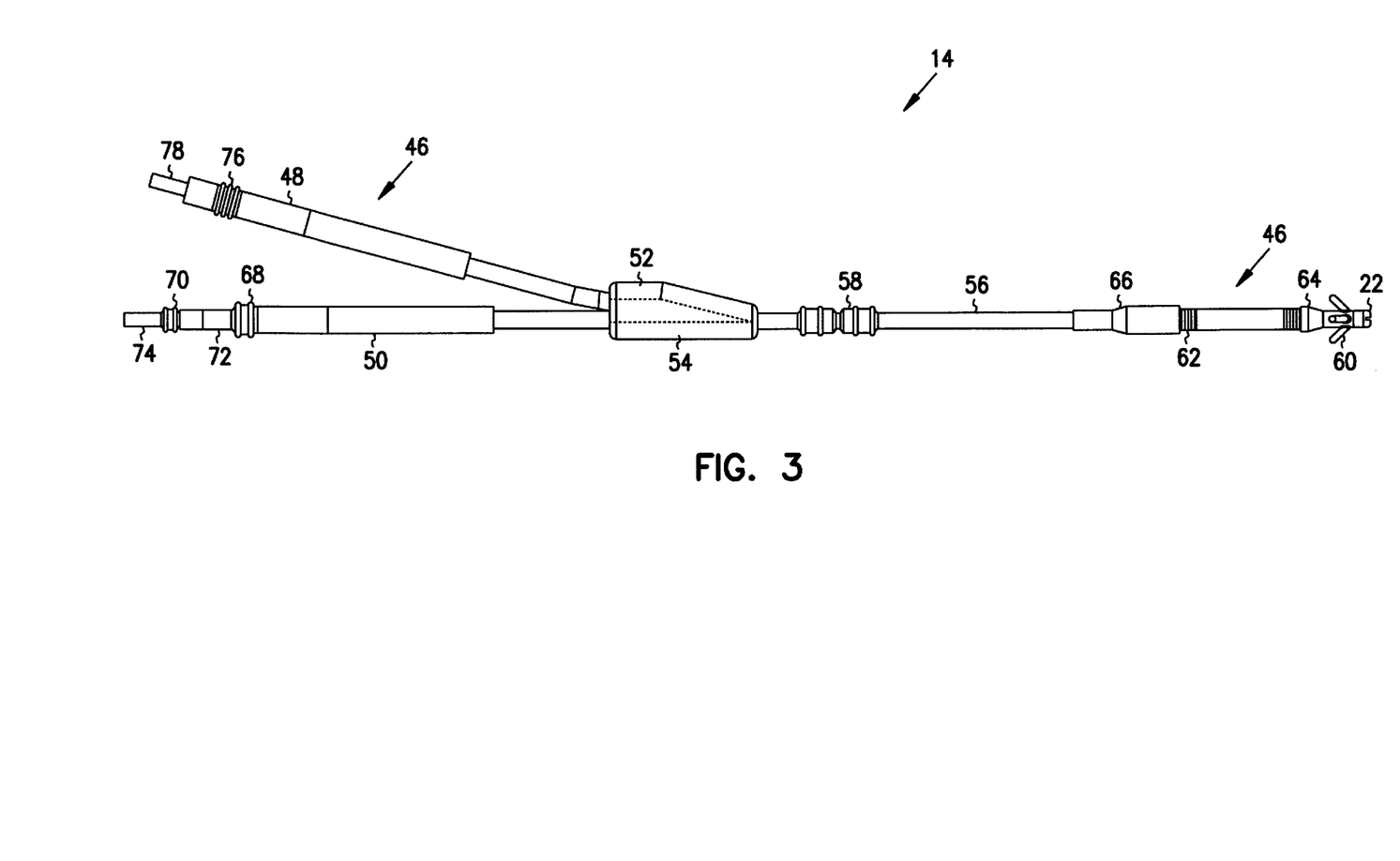
FIG. 3 is an enlarged plan view of the lead of FIG. 1.

FIG. 3 illustrates a plan view of the endocardial high voltage cable lead 14. A ventricular tip cathode or electrode 22 and shock coil 24 are located at distal end 44 of the lead 14. At a proximal end 46 of the lead there is a high voltage connector 48 and a low voltage connector 50, preferably an IS-1 (international standard one) connector. The two connectors 48, 50 are joined at a junction 52 which is covered by an insulative boot 54. A lead body 56 extends between the distal end 44 and the proximal end 46. A suture sleeve 58 is slidingly received on the lead body 56 and conventionally provides additional support for the lead 14 where it is inserted in a blood vessel of a patient. At the tip cathode 22, tines 60 may be provided to help secure the lead 14 within the heart. Other well known active or passive fixation devices, such as helical screws, may be provided. Such features are well known in the art and need not be further described herein.

The shock coil 24 comprises a segment 62 of coiled wire, preferably multifilar, more preferably tri-filar. A distal cap 64 secures one end of the segment 62, while a proximal sleeve 66 secures the other end. More detail concerning the shock coil 24 will be provided hereafter.

Regarding the proximal end 46 of the lead 14, the low voltage connector 50 is provided with annular sealing rings 68, 70 to prevent body fluids from injuring the connector, when the connector is inserted into the implantable device. Between the sealing rings 68, 70, a lead connector 72 may be provided. A pin connector 74 is located at the proximal end of the lead, thus providing two electrical contacts for the low voltage connector 50. Through these connectors 72, 74, the electrical condition of the heart may be sensed, particularly of the ventricle, if the distal end of the lead 14 is implanted therein. In addition, pacing pulses and other low voltage therapy may be provided through these connectors to the tip cathode 22. As will be more fully explained below, the shock coil 24 may be used as a low voltage anode or indifferent electrode if bipolar sensing or pacing is desired. Alternatively, a conventional low voltage ring electrode could be provided near the distal end of the lead.

The high voltage connector 48 also has annular sealing rings 76, but is usually provided only with a pin connector 78. The electrical path for high voltage shocks is usually between this pin connector 78 through an electrical conductor to the shock coil 24 and back through the heart to the can 15 of the implantable medical device 10. However, an additional coiled electrode could be provided, forming a bipolar shock electrode. Where two coiled shock electrodes are used, they are frequently placed on the lead such that one would be in the ventricle and the other in the atrium or superior vena cava. Multi-filar coiled connectors have heretofore been used to conduct the electrical current for the shock to one or more shock coils.

Figure 4:
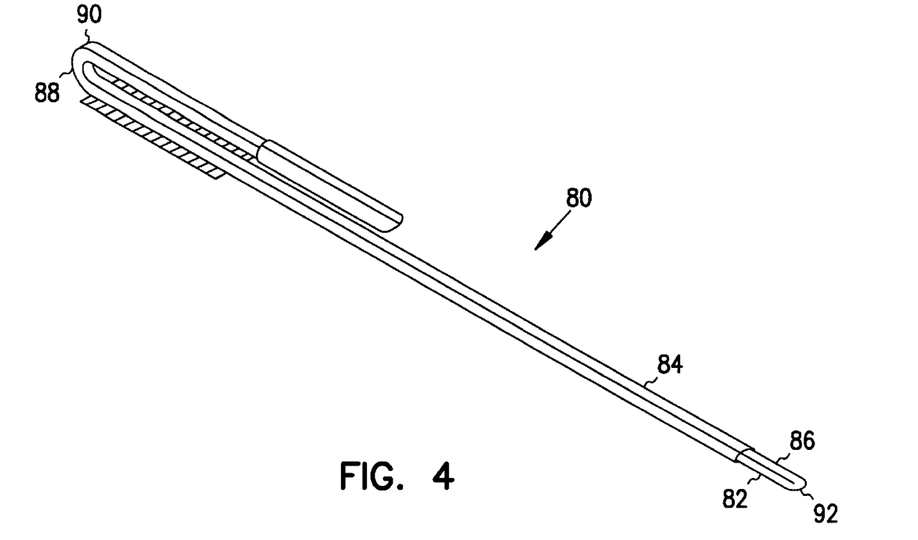
FIG. 4 is a perspective view of a cable conductor used in the lead.

In our invention, however, a looped cable conductor is provided. The cable conductor 80 of our invention is illustrated in prospective view in FIG. 4. The cable conductor 80 comprises a conductive multi-strand wire 82. In our preferred embodiment, the cable is comprised of 1 mil (one thousandth of an inch) filaments wrapped in a 7×7 configuration. That is, seven filaments are wrapped into a strand of six filaments hexagonally placed around a central filament. Then seven strands are wrapped into a cable of six strands hexagonally surrounding a central strand. The cable is insulated with ETFE polymer (expanded tetrafloroethelene). The filaments are preferably clad wire, also known as "drawn filled tube" (DFT) wire. The inner core is silver, and the outer cladding or tube is MP35N. Preferably, most of the wire 82 has insulation 84. A middle section of the wire 86 is stripped of insulation, and then the cable conductor is folded back on itself, forming a loop or bend 92 at the middle section 86. Each end 88, 90, of the conductor is also stripped of insulation. As a consequence of the looped construction described, the conductor 80 forms a redundant system, as either side of the conductor is capable of carrying current to the shock coil 24.

Figure 5:
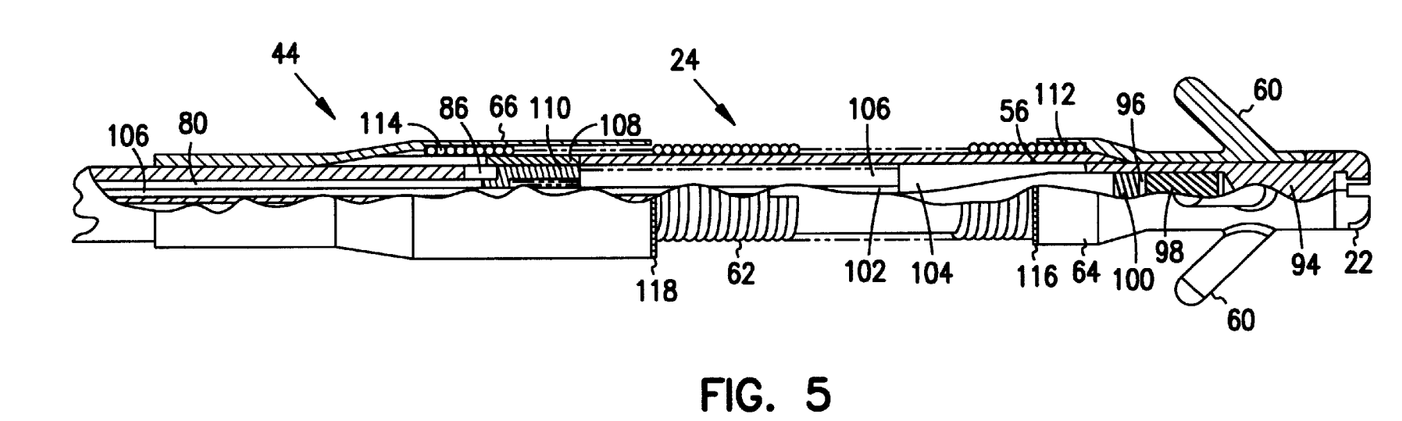
FIG. 5 is a partial section of a distal end of the lead of FIG. 3.

We will describe the distal end 44 of the lead 14 in greater detail, in connection with FIG. 5. FIG. 5 is a partial through-section of the distal end 44. As can be seen in FIG. 5, the tip cathode 22 comprises a shank 94 which extends into the distal cap 64, and into the lead body 56. The tines 60 are formed on the distal cap 64. In addition, the distal cap 64 captures a distal end 112 of the coil segment 62. Within the shank 94, a stopped bore 96 receives a crimp plug 98 and a coil conductor 100. The coil conductor 100 is a conventional low voltage conductor which extends from the tip cathode 22 to the pin connector 74 and electrically couples the cathode 22 and the pin connector 74. The shank 94 is crimped over the crimp plug 98 to secure the conductor 100 between the crimp plug and the shank.

The coil conductor 100 passes through a first lumen 102 in the lead body 56. Preferably this lumen is non-coaxial, that is, it is offset from the axis of the lead body 56. However, to receive the shank 94 symmetrically with respect to the lead body, a stopped bore 104 is provided in the distal end of the lead body. This stopped bore is coaxial with the axis of the lead body itself. A second lumen 106 is provided to receive the looped cable conductor 80. Preferably, this lumen is also non-coaxial with respect to the lead body and may be smaller in diameter than the first lumen 102. Additional lumens may be provided where additional looped cables are connected to other electrodes, such as a second shock electrode.

A window 108 cuts through a portion of the lead body 56 to expose the second lumen 106. An arcuate crimp sleeve 110 fills this window 108 and captures the stripped middle section 86 of the cable conductor 80. A more detailed description of the arcuate crimp sleeve 110 will be provided below. A proximal end 114 of the coil segment 62 extends over the arcuate crimp sleeve 110 and is covered by the proximal sleeve 66. This proximal end 114 preferably extends for a plurality of loops proximal to the arcuate crimp sleeve; preferably at least five loops, or about 6 to 10 mm. In multi-filar coils, each filer should form the loops proximal to the arcuate crimp sleeve. This extension proximal to the crimp sleeve relieves mechanical stresses, and reduces the possibility of a mechanical failure adjacent the crimp sleeve. A circumferential bead of adhesive 116 seals the distal cap 64 to the coil segment 62 and underlying lead body 56. A similar adhesive bead 118 likewise seals the proximal sleeve 66 to the coil segment 62 and lead body 56.

To assemble the looped conductor, a stylet with a small hook on one end can be inserted from the distal end of the lead body through the second lumen 106 to the proximal end of the lead body. The bend 92 in the cable conductor 80 can then be caught in the stylet, and drawn back through the lead body 56 from the proximal end to the distal end and then drawn out through the window 108. The arcuate crimp sleeve 110 is then placed on the stripped middle section 86.

Figure 6:
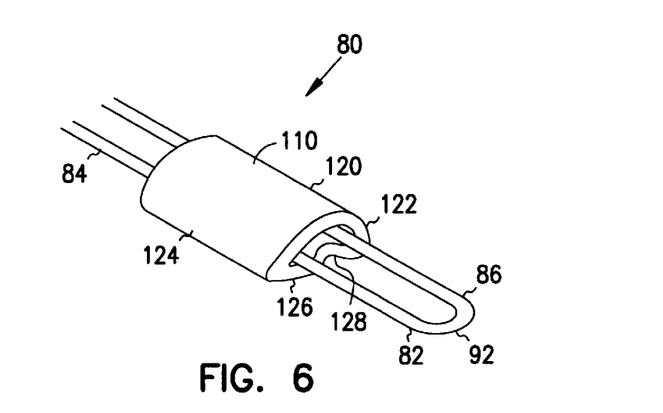
FIG. 6 is a perspective view of a distal end of the cable conductor of FIG. 4, illustrating a crimp sleeve.

The arcuate crimp sleeve 110 is illustrated in prospective view in FIG. 6. Crimp sleeve 110 comprises an outer surface 120 which is sized to have an arc or curvature conforming to the outer surface of the lead body 56. The stripped middle section 86 of the cable conductor 80 is thrust through an opening in the crimp sleeve 110 and the crimp sleeve is compressed, forming edges 122, 124, generally parallel to the cable conductor 80. On an inner surface 126, a dimple 128 is formed to compress the crimp sleeve and securely capture the stripped middle section 86 of the cable conductor, forming both a mechanical and an electrical connection.

Figure 7:
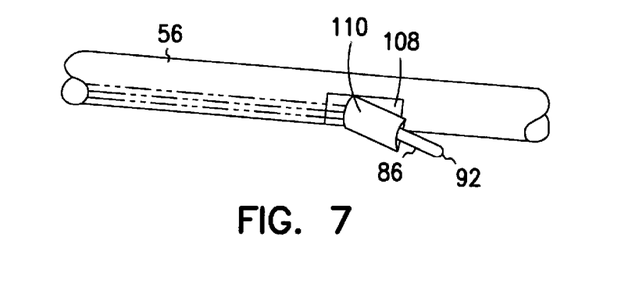
FIG. 7 is a perspective view of certain parts of the distal end of the lead, illustrating assembly of an inner insulative sleeve and cable conductor.

Once the crimp sleeve 110 is secured to the cable conductor 80, the cable conductor can be drawn back into the lead body 56, as shown in FIG. 7, positioning the crimp sleeve in the window 108. The bend 92 can be tucked back into the second lumen 106, distal from the crimp sleeve, as shown in FIG. 5, by simply deforming the lead body 56 elastically.

Figure 8:
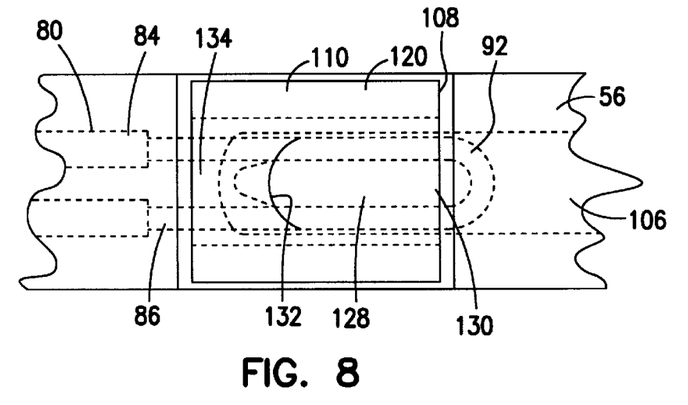
FIG. 8 is a plan view of the assembled inner sleeve and cable conductor at the crimp sleeve.
Figure 9:
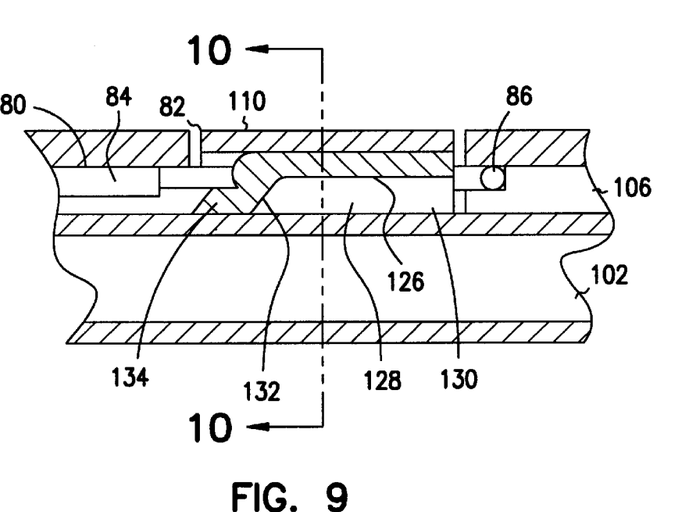
FIG. 9 is a through section of the crimp sleeve of FIG. 8, taken along line 9—9.
Figure 10:
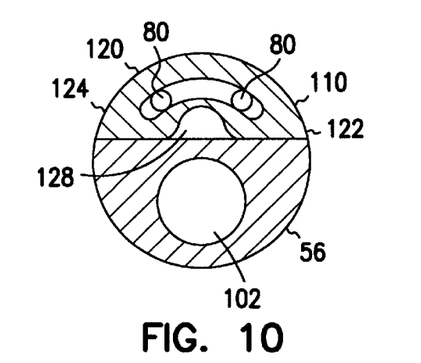
FIG. 10 is a cross section of the crimp sleeve and inner sleeve of FIGS. 8 and 9, take along line 10—10 of FIG. 8.

Further detail of the arcuate crimp sleeve can be seen in FIGS. 8, 9 and 10. FIG. 8 is a top plan view of the crimp sleeve 110, with the cable conductor 80 and dimple 128 shown in phantom lines. FIG. 9 is a plan through section of the crimp sleeve and lead body, while FIG. 10 is a cross-section of the crimp sleeve and lead body. As can be seen most clearly in FIGS. 8 and 9, the dimple 128 extends from a distal end 130, but does not extend the entire length of the crimp sleeve 110. Rather, there is a radiused transition 132 and an uncrimped proximal end 134 on the crimp sleeve. The radiused transition 132, formed in the inner surface 126 of the crimp sleeve 110, reduces the mechanical stress on the cable conductor, by lowering the stress risers at this junction.

In FIG. 10, it can be readily seen that the outer surface 120 of the crimp sleeve conforms to the outer surface of the lead body 56. The coiled segment 62 is placed on the lead body with the proximal end extending past the crimp sleeve 110. The coil 62 is laser welded to the crimp sleeve. The proximal sleeve 66 is slid up over the proximal end of the coil 62 and secured with adhesive, as described above.

Figure 11:
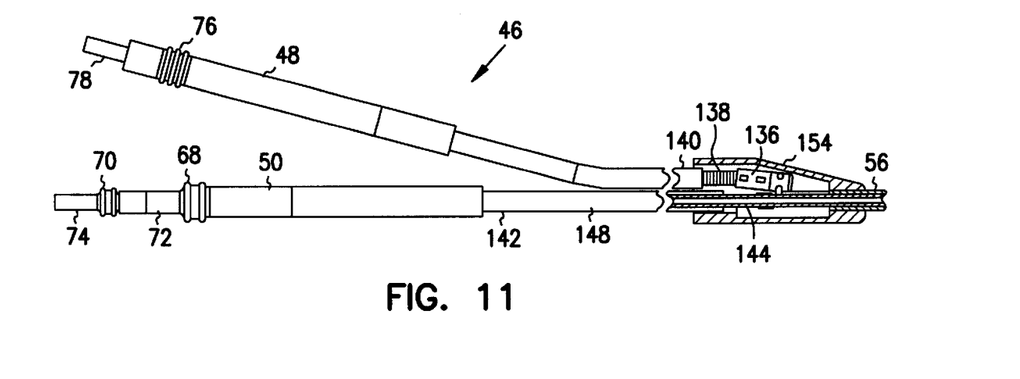
FIG. 11 is a partial through section of the proximal end of the lead.
Figure 12:
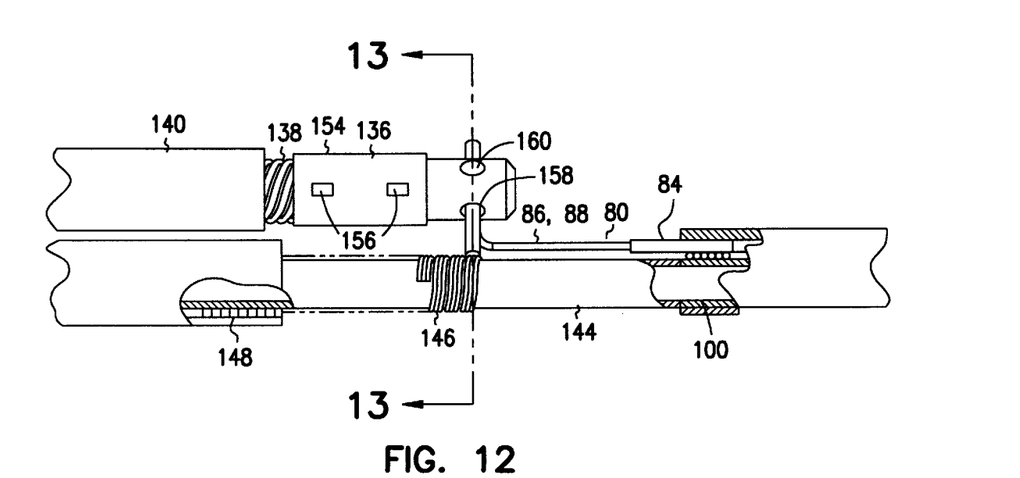
FIG. 12 is an enlarged partial section view of a junction shown in FIG. 11.
Figure 13:
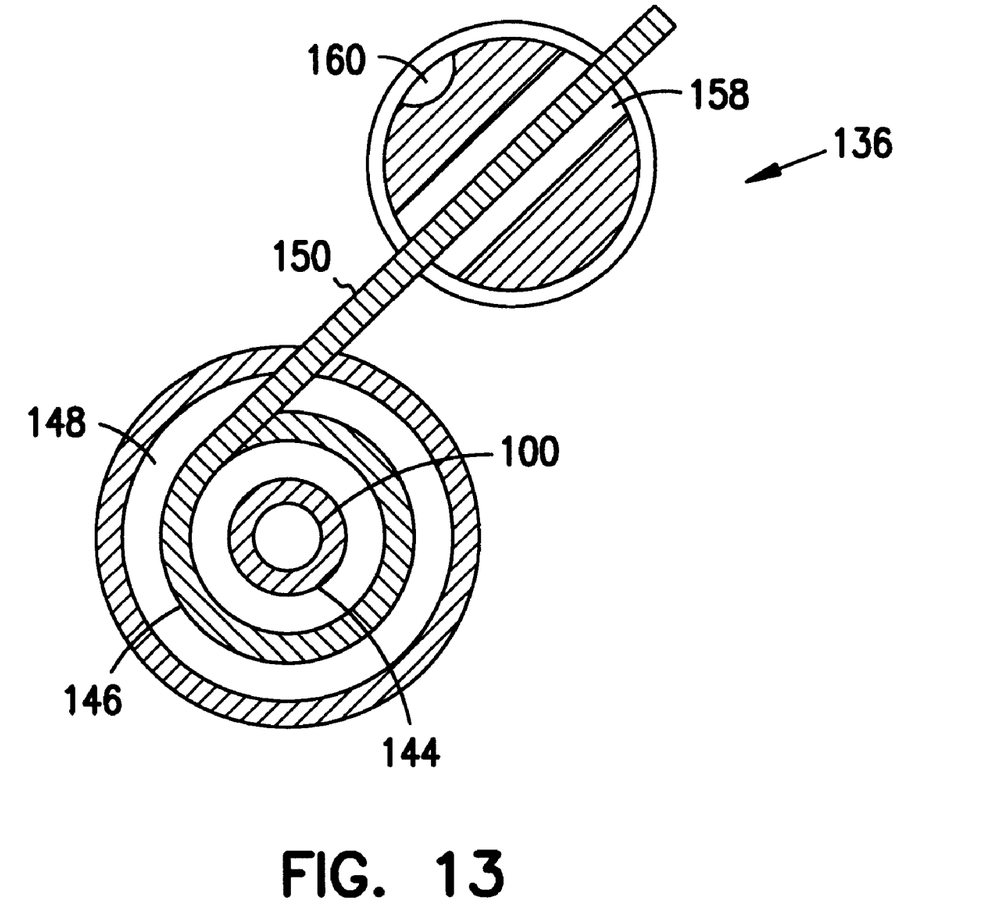
FIG. 13 is a cross section of the junction of FIG. 12, taken along line 13—13.

The proximal end 46 of the lead is shown in detail in FIGS. 11, 12 and 13. FIG. 11 shows a partial through section of a plan view of the distal end 46 of the lead. The boot 54 encloses an assembly connecting the two connectors 48, 50. A crimp connector 136 is connected to a coiled conductor 138 which is electrically and mechanically connected to the pin connector 78 of the high voltage connector 48. The coil conductor 138 passes through an insulating sleeve 140. The low voltage connector 50 has a coaxial lead segment 142. The coil conductor 100, described above in connection with the distal end of the lead, passes co-axially down the lead segment 142, that is, the axis of the coil 100 and the axis of the lead segment 142 coincide. An inner tubing 144 surrounds the coil conductor 100. A return low voltage coil conductor 146 surrounds the inner tubing 144 and is connected proximally at one end to the ring connector 72 and at a distal end 150 to the crimp connector 136. An outer tubing 148 encases the return coil 146.

Details of the crimp connector 136 can be seen in FIG. 12. The crimp connector 136 has a plug 152 which is substantially cylindrical shape and fits, at one end thereof, within the high voltage conductor coil 138. A sleeve 154 surrounds the end of the high voltage conductor coil 138 and one end of the plug 152. The sleeve 154 is crimped at 156 to secure the plug to the coil 138. A through bore 158 extends through an exposed part of the plug 152. The exposed ends 86, 88, of the looped cable conductor 80 are passed into this through bore 158, together with the distal end 150 of the return low voltage coil 146. A crimp 160 secures these ends 86, 88, 150 within the plug.

In the illustrated embodiment, the looped cable conductor is used both to conduct high voltage shocks delivered through the coil conductor 138 of the high voltage connector 48, and to act as a return path for low voltage pacing pulses delivered through the inner coil 100 and catholic tip 22, when a bipolar configuration is desired. Through this same low voltage connection, the looped cable conductor also forms part of the electrical path for sensing the electrical condition of the heart.

Those skilled in the art will recognize from the foregoing description that the looped cable conductor of our invention can be used in cardiac leads in other configurations without departing from the teachings of our invention. For example, more then one looped cable conductor could be provided for bipolar defibrillation shocks. Low voltage connections could be provided to some, all or none of such looped cable conductors.

While preferred embodiments of the present invention have been shown and described, modifications thereof can be made by one skilled in the art without departing from the spirit or teachings of this invention. The embodiments described herein are exemplary only and are not limiting. Many variations and modifications of this system and apparatus are possible and are within the scope of the invention. Accordingly, the scope of protection is not limited to the embodiments described herein, but is only limited by the claims which follow, the scope of which shall include all equivalents of the subject matter of the claims.

What is claimed is:

1. An implantable cardiac stimulation lead comprising
   an elongated lead body having a proximal and a distal end;
   an electrical connector at said proximal end;
   a first electrode near said distal end, and
   an electrical conductor electrically connecting said electrical connector and said electrode, said conductor comprising
      a conductive wire having a first end and a second end, said wire being folded into a bend at a point substantially midway along said wire and positioned in said lead body such that said bend is near one end of said lead body and both said first and second ends are near the other end of said lead body.

2. The implantable cardiac stimulation lead according to claim 1 wherein said conductive wire comprises a plurality of filaments.

3. The implantable cardiac stimulation lead according to claim 2 wherein said conductive wire comprises a cable.

4. The implantable cardiac stimulation lead according to claim 1 wherein said conductive wire is coated by an insulative sleeve and said conductive wire is exposed through said sleeve at said bend and at said ends.

5. The implantable cardiac stimulation lead according to claim 1 further comprising a window near said distal end of said lead body and a connector connected to said wire and exposed through said window.

6. The implantable cardiac stimulation lead according to claim 5 wherein said connector is connected to said wire near said bend.

7. The implantable cardiac stimulation lead according to claim 5 wherein said connector is a crimp sleeve.

8. The implantable cardiac stimulation lead according to claim 7 wherein said crimp sleeve has an outer surface exposed through said window and said outer surface has an arcuate shape conforming subsantially to an outer surface of said lead body.

9. The implantable cardiac stimulation lead according to claim 8 wherein said crimp sleeve has a length subsantially parallel to said conductors and is crimped along only part of said length.

10. The implantable cardiac stimulation lead according to claim 9 wherein said crimp sleeve has a radiused area proximal along said length adjacent said wire.

11. The implantable cardiac stimulation lead according to claim 10 wherein said radiused area is formed by crimping.

12. The implantable cardiac stimulation lead according to claim 5 wherein said electrode comprises a shock coil having a distal end and a proximal end and at least one filar coiled between said ends.

13. The implantable cardiac stimulation lead according to claim 12 wherein coil has at least one loop proximal to said connector and a plurality of loops distal from said connector and wherein said coil is electrically and mechanically connected to said connector.

14. The implantable cardiac stimulation lead according to claim 1 further comprising
   a stimulation electrode at said distal end of said lead body;
   a low-voltage connector at said proximal end of said lead;
   an electrical conductor electrically connecting said stimulation electrode and said low-voltage connector.

15. The implantable cardiac stimulation lead according to claim 14 wherein said first electrode comprises a defibrillation coil electrode and said electrical connector is a high voltage connector.

16. The implantable cardiac stimulation lead according to claim 15 wherein said conductive wire is further connected to a second low voltage connector, said connector being at said proximal end of said lead body.

17. The implantable cardiac stimulation lead according to claim 16 comprising a crimp connector at a proximal end of said conductive wire, said crimp connector connecting said conductive wire and a first conductor connected to said high voltage connector and a second conductor connected to said low voltage connector.

18. An implantable cardiac stimulation system comprising
   a hermetically sealed can containing
      a power source;
      a control circuit connected to said power source;
      a sense circuit capable of detecting the electrical condition of the heart;
      a stimulus generator capable of producing an electrical output to stimulate the heart as controlled by said control circuit; and
   a lead connected to said generator, said lead comprising
      an elongated lead body having a proximal and a distal end;
      an electrical connector at said proximal end;
      a first electrode near said distal end, and
      an electrical conductor electrically connecting said electrical connector
   and said electrode, said conductor comprising
      a conductive wire having a first end and a second end, said wire being folded into a bend at a point substantially midway along said wire and positioned in said lead body such that said bend is near one end of said lead body and both said first and second ends are near the other end of said lead body.

19. The implantable cardiac stimulation system according to claim 18 wherein said conductive wire comprises a plurality of filaments.

20. The implantable cardiac stimulation system according to claim 19 wherein said conductive wire comprises a cable.

21. The implantable cardiac stimulation system according to claim 18 wherein said conductive wire is coated by an insulative sleeve and said conductive wire is exposed through said sleeve at said bend and at said ends.

22. The implantable cardiac stimulation system according to claim 18 further comprising a window near said distal end of said lead body and a connector connected to said wire and exposed through said window.

23. The implantable cardiac stimulation system according to claim 22 wherein said connector is connected to said wire near said bend.

24. The implantable cardiac stimulation system according to claim 22 wherein said connector is a crimp sleeve.

25. The implantable cardiac stimulation system according to claim 24 wherein said crimp sleeve has a n outer surface exposed through said window and said outer surface has an arcuate shape conforming subsantially to an outer surface of said lead body.

26. The implantable cardiac stimulation system according to claim 25 wherein said crimp sleeve has a length subsantially parallel to said conductors and is crimped along only part of said length.

27. The implantable cardiac stimulation system according to claim 26 wherein said crimp sleeve has a radiused area proximal along said length adjacent said wire.

28. The implantable cardiac stimulation system according to claim 27 wherein said radiused area is formed by crimping.

29. The implantable cardiac stimulation system according to claim 22 wherein said electrode comprises a shock coil having a distal end and a proximal end and at least one filar coiled between said ends.

30. The implantable cardiac stimulation system according to claim 29 wherein coil has at least one loop proximal to said connector and a plurality of loops distal from said connector and wherein said coil is electrically and mechanically connected to said connector.

31. The implantable cardiac stimulation system according to claim 18 further comprising a stimulation electrode at s aid distal end of said lead body;

a low-voltage connector at said proximal end of said lead;

an electrical conductor electrically connecting said stimulation electrode and said low-voltage connector.

32. The implantable cardiac stimulation system according to claim 31 wherein said first electrode comprises a defibrillation coil electrode and said electrical connector is a high voltage connector.

33. The implantable cardiac stimulation system according to claim 32 wherein said conductive wire is further connected to a second low voltage connector, said connector being at said proximal end of said lead body.

34. The implantable cardiac stimulation system according to claim 33 comprising a crimp connector at a proximal end of said conductive wire, said crimp connector connecting said conductive wire and a first conductor connected to said high voltage connector and a second conductor connected to said low voltage connector.

* * * * *

UNITED STATES PATENT AND TRADEMARK OFFICE
CERTIFICATE OF CORRECTION

PATENT NO.: 6,104,961

DATED: Aug. 15, 2000

INVENTOR(S): Conger et al.

It is certified that error appears in the above-identified patent and that said Letters Patent is hereby corrected as shown below:

In column 1, line 9, delete "particularity" and insert --particularly--, therefor.

In column 1, line 40, delete "defibillation" and insert --defibrillation--, therefor.

In column 4, line 1, delete "cardioverterldefibrillator" and insert --cardioverter/defibrillator--, therefor.

In column 6, lines 27-28, delete "can 15" and insert --can 16--, therefor.

In column 9, line 48, delete "subsantially" and insert --substantially--, therefor.

In column 10, line 60, delete "a n" and insert --an--, therefor.

In column 10, line 62, delete "subsantially" and insert --substantially--, therefor.

In column 10, lines 65-66, delete "subsantially" and insert --substantially--, therefor.

In column 11, line 18, delete "s aid" and insert --said--, therefor.

Signed and Sealed this

Twenty-fourth Day of April, 2001

*Attest:*

NICHOLAS P. GODICI

*Attesting Officer*     *Acting Director of the United States Patent and Trademark Office*